(12) United States Patent
Zhang et al.

(10) Patent No.: US 10,053,665 B2
(45) Date of Patent: Aug. 21, 2018

(54) CELL MAGNETIC SORTING SYSTEM, SORTING APPARATUS, AND TREATMENT DEVICE

(71) Applicant: SHENZHEN CYTOROLA BIOMEDICAL TECH CO., LTD., Shenzhen, Guangdong (CN)

(72) Inventors: Lifeng Zhang, Guangdong (CN); Shubo Wan, Guangdong (CN); Hua Wang, Guangdong (CN)

(73) Assignee: SHENZHEN CYTOROLA BIOMEDICAL TECH CO., LTD., Shenzhen (CN)

( * ) Notice: Subject to any disclaimer, the term of this patent is extended or adjusted under 35 U.S.C. 154(b) by 27 days.

(21) Appl. No.: 15/214,440

(22) Filed: Jul. 19, 2016

(65) Prior Publication Data
US 2016/0340637 A1    Nov. 24, 2016

Related U.S. Application Data

(63) Continuation of application No. PCT/CN2014/073544, filed on Mar. 17, 2014.

(30) Foreign Application Priority Data

Jan. 23, 2014  (CN) .......................... 2014 1 0033585

(51) Int. Cl.
*B03C 1/24* (2006.01)
*C12M 1/00* (2006.01)
(Continued)

(52) U.S. Cl.
CPC ............. *C12M 47/04* (2013.01); *B03C 1/002* (2013.01); *B03C 1/01* (2013.01); *B03C 1/03* (2013.01);
(Continued)

(58) Field of Classification Search
CPC ......... B03C 1/03; B03C 1/033; B03C 1/0335; B03C 1/24; B03C 1/288; B03C 1/32;
(Continued)

(56) References Cited

U.S. PATENT DOCUMENTS 4,144,163 A * 3/1979 Kolm ........................ B03C 1/03
209/12.2
4,153,542 A * 5/1979 Bender ..................... B03C 1/03
209/11
(Continued)

FOREIGN PATENT DOCUMENTS

CN  101019026 A  8/2007

OTHER PUBLICATIONS

International Search Report of PCT Patent Application No. PCT/CN2014/073544 dated Dec. 19, 2014.
(Continued)

*Primary Examiner* — Joseph C Rodriguez

(57) ABSTRACT

A cell magnetic sorting system comprises a continuous magnetic cell sorting apparatus. The continuous magnetic cell sorting apparatus comprises a rotating magnetic field generator, a forward solenoid and a reverse solenoid; the forward solenoid and the reverse solenoid surround the rotating magnetic field generator in forward and reverse directions, one end of the forward solenoid is connected to a cell solution source, the other end of the forward solenoid is connected to one end of the reverse solenoid through a T-shaped tube, an inlet of a T-shaped tube is connected to an outlet of the forward solenoid, a first outlet of the T-shaped tube is connected to an inlet of the reverse solenoid, a second outlet of the T-shaped tube is connected to an inlet of the target cell collection container.

9 Claims, 3 Drawing Sheets

(51) Int. Cl.
*B03C 1/00* (2006.01)
*B03C 1/01* (2006.01)
*B03C 1/03* (2006.01)
*B03C 1/033* (2006.01)
*B03C 1/28* (2006.01)
*G01N 15/10* (2006.01)
*G01N 35/00* (2006.01)

(52) U.S. Cl.
CPC .............. *B03C 1/0335* (2013.01); *B03C 1/24* (2013.01); *B03C 1/288* (2013.01); *G01N 15/1031* (2013.01); B03C 2201/18 (2013.01); B03C 2201/26 (2013.01); G01N 35/0098 (2013.01); G01N 2015/1006 (2013.01); G01N 2015/1081 (2013.01)

(58) Field of Classification Search
CPC ............ B03C 2201/18; B03C 2201/22; B03C 2201/26; C12M 47/04; G01N 15/1031; G01N 2015/149; G01N 2015/1006; G01N 2015/1081; G01N 35/0098
See application file for complete search history.

(56) References Cited

U.S. PATENT DOCUMENTS

| | | | | |
|---|---|---|---|---|
| 4,395,746 | A * | 7/1983 | Tanaka | B03C 1/24 134/1 |
| 6,482,328 | B1 * | 11/2002 | Davidson | B03C 1/005 209/215 |
| 8,343,440 | B2 * | 1/2013 | Yoshioka | C01N 33/57492 422/502 |
| 8,715,494 | B2 * | 5/2014 | Danov | B03C 1/0335 209/227 |
| 9,126,206 | B2 * | 9/2015 | Hartmann | B03C 1/253 |
| 9,156,037 | B2 * | 10/2015 | Yung | B03C 1/01 |
| 9,238,791 | B2 * | 1/2016 | Yoshioka | C01N 33/57492 |
| 9,546,392 | B2 * | 1/2017 | Lamish | B03C 1/0335 |
| 2007/0238169 | A1 * | 10/2007 | Abilez | C12M 25/14 435/325 |
| 2009/0047297 | A1 * | 2/2009 | Kim | B03C 1/288 424/184.1 |
| 2012/0077267 | A1 * | 3/2012 | Lee | C12M 47/04 435/325 |

OTHER PUBLICATIONS

1st Office Action of counterpart Chinese Patent Application No. 201410033585.7 dated Nov. 24, 2014.

* cited by examiner

CELL MAGNETIC SORTING SYSTEM, SORTING APPARATUS, AND TREATMENT DEVICE

CROSS REFERENCE TO RELATED APPLICATIONS

This application is a continuation application of PCT/CN2014/073544 filed on Mar. 17, 2014, which claims the priority of China patent application No. 201410033585.7 filed on Jan. 23, 2014. The contents of the above-mentioned applications are all hereby incorporated by reference.

BACKGROUND OF THE INVENTION

Field of the Invention

The present application relates to a cell magnetic sorting system, a sorting apparatus and a treatment device.

Related Arts

A magnetic material can be specifically bound with target cells through biotechnology, and using an electromagnetic method to sort out target cells of high specificity (target cell) by utilizing the magnetism of magnetically labeled target cells is a key step of cell medicine and cell research activities. Existing cell sorting schemes and cell sorting apparatuses have the defects of complex operation, low sorting efficiency, low sorting purity, poor sorting environment control, etc.

SUMMARY OF THE INVENTION

The object of the present application is to provide a cell magnetic sorting system in order to overcome the defects of the prior art, and the magnetic cell sorting system is structurally simple, highly efficient, reliable and suitable for continuous separation, can prevent environmental factors from polluting an operation process, and can realize high-quality cell sorting.

Another object of the present application is to provide a magnetic cell sorting apparatus for the magnetic cell sorting system.

Yet another object of the present application is to provide a treatment device with the magnetic cell sorting system.

In order to achieve the foregoing objects, the present application adopts the following technical solutions:

A cell magnetic sorting system comprises a cell solution source, a solution driving device, a continuous magnetic cell sorting apparatus, a target cell collection container, a residual solution collection container and a control unit, where the continuous magnetic cell sorting apparatus comprises a rotating magnetic field generator, a forward solenoid and a reverse solenoid, the forward solenoid and the reverse solenoid surround the rotating magnetic field generator in forward and reverse directions, one end of the forward solenoid is connected to a solution outlet of the cell solution source, the other end of the forward solenoid is connected to one end of the reverse solenoid through a T-shaped tube, an inlet of the T-shaped tube is connected to the outlet of the forward solenoid, a first outlet of the T-shaped tube is connected to an inlet of the reverse solenoid, a second outlet of the T-shaped tube is connected to an inlet of the target cell collection container, the direction of the second outlet is consistent with the winding direction of the forward solenoid, the direction of the first outlet is opposite to the winding direction of the forward solenoid, and the control unit is connected to the continuous magnetic cell sorting apparatus and the solution driving device through control lines, and is configured to control the continuous magnetic cell sorting apparatus to generate a magnetic acting force and control the solution driving device to drive a solution in the cell solution source, so that unlabeled cells and magnetically labeled cells respectively flow into the residual solution collection container and the target cell collection container through the T-shaped tube.

Starting parts of the inlet, the first outlet and the second outlet of the T-shaped tube are provided with flow-stopping switches.

The magnetic cell sorting apparatus further comprises a device that is connected with the second outlet of the T-shaped tube and is for applying a negative pressure to the second outlet.

The solution driving device adopts solution line peristaltic driving, and comprises a primary solution pump arranged between the cell solution source and the continuous magnetic cell sorting apparatus and a secondary pump arranged between the continuous magnetic cell sorting apparatus and the target cell collection container.

The control unit comprises a solution flow velocity controller connected to the solution driving device and a magnetic field controller connected to the continuous magnetic cell sorting apparatus through the control lines, and the solution flow velocity controller and the magnetic field controller control the unlabeled cells and the magnetically labeled cells to move in opposite directions at the second outlet of the T-shaped tube to complete sorting of the magnetically labeled cells.

A treatment device comprises the magnetic cell sorting system.

A magnetic cell sorting apparatus comprises a rotating magnetic field generator, a forward solenoid and a reverse solenoid, the forward solenoid and the reverse solenoid surround the rotating magnetic field generator in forward and reverse directions, one end of the forward solenoid is connected to a solution outlet of the cell solution source, the other end of the forward solenoid is connected to one end of the reverse solenoid through the T-shaped tube, an inlet of the T-shaped tube is connected to an outlet of the forward solenoid, a first outlet of the T-shaped tube is connected to an inlet of the reverse solenoid, a second outlet of the T-shaped tube is connected to an inlet of the target cell collection container, the direction of the second outlet is consistent with the winding direction of the forward solenoid, and the direction of the first outlet is opposite to the winding direction of the forward solenoid.

Starting parts of the inlet, the first outlet and the second outlet of the T-shaped tube are provided with flow-stopping switches.

The magnetic cell sorting apparatus further comprises a device that is connected with the second outlet of the T-shaped tube and is for applying a negative pressure to the second outlet.

The present application has the following advantages:

The design of the rotating magnetic field generator, the forward solenoid and the reverse solenoid in forward and reverse directions ingeniously realizes the reverse helical movement of magnetically labeled cells opposite to the flowing direction of a liquid, moreover, the design of the T-shaped tube ingeniously enables the magnetically labeled cells to move into the target cell collection container in a direction opposite to the flowing direction of the solution under the action of magnetic force, unlabeled cells move into the residual solution collection container along the flowing direction of the solution, uninterrupted continuous magnetically labeled cell sorting is realized, consequently, sorting time is shortened, and clinical level mass cell separation is benefited. The solution flow velocity controller and the magnetic field controller respectively control the unlabeled cells and the magnetically labeled cells to move in opposite directions to complete sorting of the magnetically labeled cell.

By controlling the opposite-direction movement of an electromagnetic fluid and a solution fluid, solution transfer and sorting are performed at the same time, rapid and effective cell separation is realized, and cell sorting quality can be increased; the reverse solenoid design can help to increase the number of sorted cells and the purity of the sorted cells; the systems can be cascaded, so that continuous secondary sorting or continuous cell cleaning can be realized, and sorting time can be shortened.

The present application is structurally simple, highly efficient and reliable, sorting is performed in a sealed duct, consequently, environmental factors can be prevented from polluting the operation process, a large number of high-purity sorted cell products can be obtained, and the sorting of clinical level cell products is benefited.

Further, by arranging the flow-stopping switches at the starting parts of the inlet and outlets of the T-shaped tube, the control unit can conveniently control the rinsing and recovery of the target cells by means of the control lines, realizing the one-step completion of a cell separation, rinsing, recovery and filling process.

DETAILED DESCRIPTION OF THE INVENTION

The present application is further described in detail by means of embodiments with reference to accompanying drawings in the following.

Figure 1:
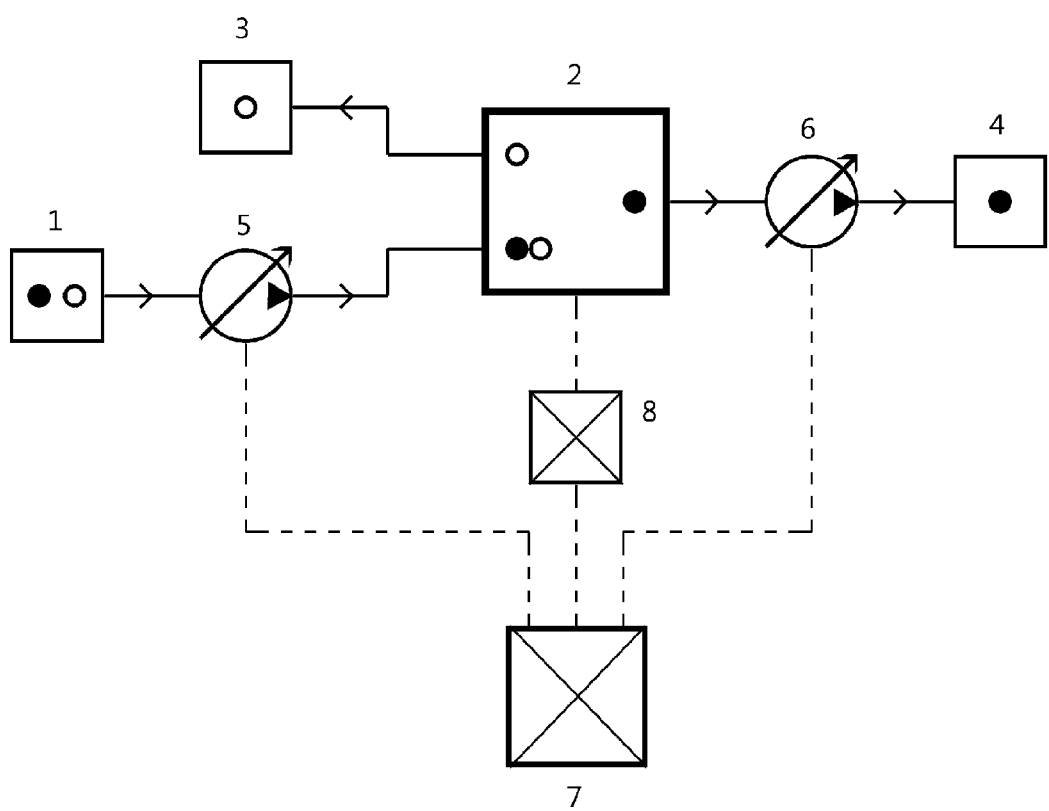
FIG. 1 is a structural schematic diagram of an embodiment of a cell magnetic sorting system of the present application.
Figure 2:
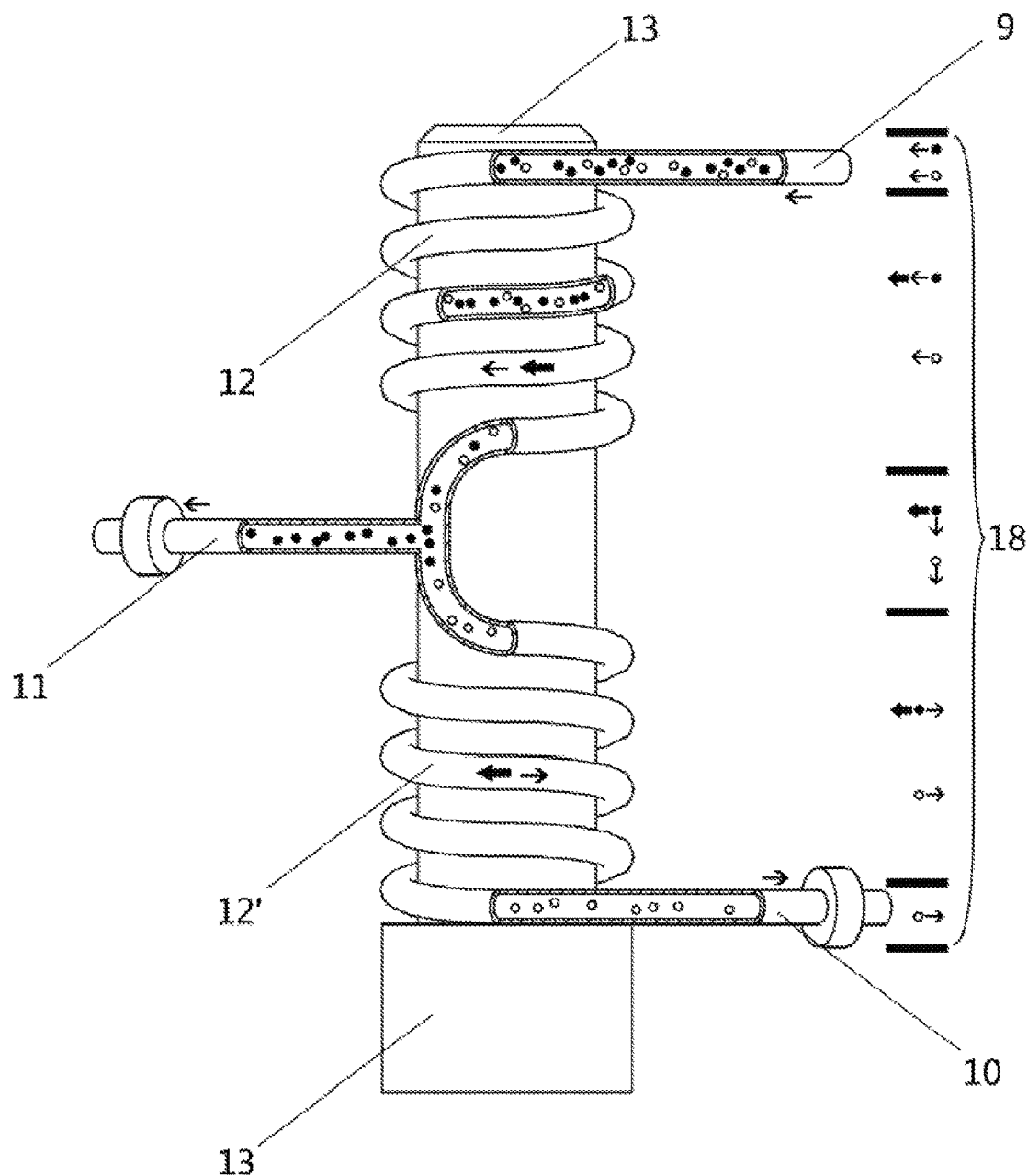
FIG. 2 is a structural schematic diagram of an embodiment of a continuous magnetic cell sorting apparatus of the present application.
Figure 3:
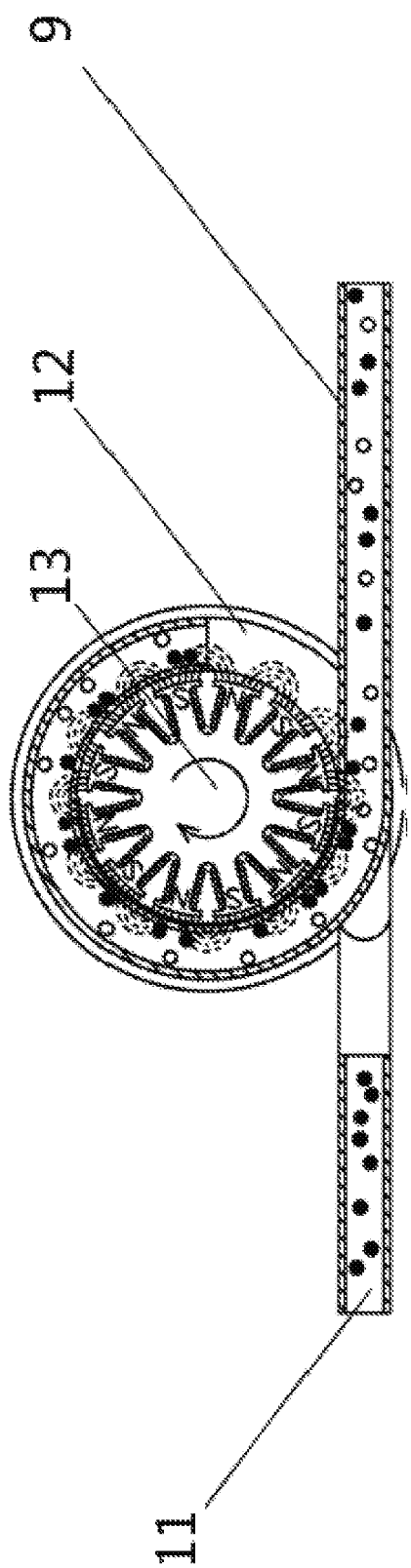
FIG. 3 is a vertical view of the continuous magnetic cell sorting apparatus shown in FIG. 2.

Referring to FIG. 1 to FIG. 3, in some embodiments, a cell magnetic sorting system comprises a cell solution source 1, a continuous magnetic cell sorting apparatus 2, a residual solution collection container 3, a target cell collection container 4, a primary solution pump 5, a secondary solution pump 6, a solution flow velocity controller 7, and a magnetic field controller 8. The continuous magnetic cell sorting apparatus 2 comprises a rotating magnetic field generator 13, a forward solenoid 12, a reverse solenoid 12', and a T-shaped tube 11, the forward solenoid 12 and the reverse solenoid 12' surround the rotating magnetic field generator 13 in forward and reverse directions, and the T-shaped tube 11 is connected between the forward solenoid 12 and the reverse solenoid 12'. The cell solution source 1 is connected to a solution inlet of the continuous magnetic cell sorting apparatus 2 through the primary solution pump 5, a residual solution outlet of the continuous magnetic cell sorting apparatus 2 is connected to the residual solution collection container 3, and a second outlet of the T-shaped tube 11 of the continuous magnetic cell sorting apparatus 2 which is a sorting outlet is connected to the target cell collection container 4 through the secondary solution pump 6. The control lines of the solution flow velocity controller 7 are connected to the primary solution pump 5 and the secondary solution pump 6. The control line of the magnetic field controller 8 is connected to the continuous magnetic cell sorting apparatus 2.

When in use, the solution flow velocity controller 7 controls the primary solution pump 5 to suck magnetically labeled cell solution from the cell solution source 1 and inject the magnetically labeled cell solution into the continuous magnetic cell sorting apparatus 2, and the control line of the magnetic field controller 8 controls the rotating magnetic field generator 13 of the continuous magnetic cell sorting apparatus 2 to generate a rotating magnetic field, which applies a magnetic rotating acting force on the magnetically labeled cells flowing into the solenoids, so that the reverse helical movement of the magnetically labeled cells opposite to the flowing direction of the liquid realizes target cell sorting. The solution flow velocity controller 7 drives the secondary solution pump 6 to transfer the sorted target cell solution into the target cell collection container 4, and remaining residual solution is guided into the residual solution collection container 3.

Besides providing driving force for sucking the solution from the cell solution source 1 and injecting the solution into the continuous magnetic cell sorting apparatus 2, the primary solution pump 5 also provides driving force for pushing the cell solution to be separated and then injecting the target cell solution and the residual solution into the target cell collection container 4 and the residual solution collection container 3. The driving force provided by the secondary solution pump 6 can compensate the flow velocity of the separated target cell solution in order to increase cell separation efficiency. By adding the secondary solution pump 6 and controlling the secondary solution pump 6 to cooperate with the primary solution pump 5 to do cooperative work, the sorting speed and sorting quality of the target cells can be increased.

Referring to FIG. 2 and FIG. 3, in some embodiments, in the continuous magnetic cell sorting apparatus 2, one end of the forward solenoid 12 serves as a solution inlet 9 connected to the cell solution source 1, the other end of the forward solenoid 12 is connected to one end of the reverse solenoid 12' through the T-shaped tube 11, the other end of the reverse solenoid 12' serves as a solution outlet 10 connected to the residual solution collection container 3, the two opposite ends of the T-shaped tube 11 are respectively connected to the forward solenoid 12 and the reverse solenoid 12', a first outlet of the T-shaped tube 11 is connected to the inlet of the reverse solenoid 12', the direction of the first outlet is opposite to the winding direction of the forward solenoid 12, the direction of a second outlet of the T-shaped tube 11 is consistent with the winding direction of the forward solenoid 12, and the second outlet of the T-shaped tube 11 is a sorting outlet connected to the target cell collection container 4. In the operation process, under the control of the magnetic field controller, the rotating magnetic field which is generated in the forward solenoid 12 and the reverse solenoid 12' by the rotating magnetic field part 13 attracts and moves target cells, the magnetically labeled target cells are accelerated under the action of the magnetic field to move toward the sorting outlet of the T-shaped tube 11 in the section of the forward solenoid 12, i.e., at the forward stage of the solenoid, the magnetically labeled target cells move toward the sorting outlet of the T-shaped tube 11 in a direction opposite to the flowing direction of the liquid under the action of the magnetic field in the section of the reverse solenoid 12', i.e., at the reverse stage of the solenoid, and thereby the magnetically labeled target cells are enriched at the sorting outlet of the T-shaped tube 11 and separated and discharged into the target cell collection container 4.

Referring to FIG. 2, the pattern represented by the mark number 18 shows the stress states of the magnetically labeled cells and the unlabeled cells at each stage in the continuous magnetic cell sorting apparatus 2. In the figure, the black solid rounds represent the magnetically labeled cells, the hollow rounds represent the unlabeled cells, the thin arrows represent the flowing force of the liquid, and the thick arrows represent magnetic acting force. The cell solution is inputted into the solution inlet 9, wherein the magnetically labeled target cells rapidly arrive at the T-shaped tube under the joint action of the forward solenoid 12 and the rotating magnetic field 5, the joint action of the reverse solenoid 12' and the rotating magnetic field 5 generate resistance to the magnetically labeled cells, stopping the magnetically labeled cells from continuing to flow out along the solenoid, and thus the magnetically labeled cells can be enriched at the T-shaped tube 11 and discharged from the sorting outlet. When the switch of the starting part of the second outlet of the T-shaped tube is closed, the solenoids can be flushed bidirectionally; when the switch of the starting part of the first outlet of the T-shaped tube is closed, the target cells of the second outlet duct of the T-shaped tube and the cell collection container can be rinsed and filled; an appropriate negative pressure can be applied at the sorting outlet of the T-shaped tube 11 in order to bring out the enriched target cells. In addition, because the magnetic field does not have a magnetic force effect on the magnetically unlabeled cells, the phenomenon that the magnetically unlabeled cells are accelerated by the forward solenoid 12, stopped by the reverse solenoid 12' and enriched at the T-shaped tube cannot take place, and therefore the magnetically unlabeled cells can be smoothly guided out of the solution outlet 10 through the reverse solenoid 12'.

The control line of the magnetic field controller 8 can also be connected to the solution flow velocity controller 7, and the solution flow velocity controller 7 and the magnetic field controller 8 can coordinatively drive the continuous magnetic cell sorting apparatus 2, achieving a highly efficient, high-quality cell sorting effect.

Other embodiments relate to a treatment device, the treatment device can be various apparatuses for cell medicine or cell research, and the treatment device can be provided with the magnetic cell sorting system of any above-mentioned embodiment.

Although the present application is described above in further detail through specific embodiments, the present application is not limited to the specific embodiments. For example, those skilled in the art can understand that besides adopting the solution pumps, the devices providing flowing force for liquid also can adopt any other equipment which can drive the liquid to flow. It should be understood by persons of ordinary skill in the art that any simple deduction or replacement made without departing from the spirit of the present application shall fall within the protection scope of the present application.

What is claimed is:

1. A cell magnetic sorting system, comprising a cell solution source, a solution driving device, a continuous magnetic cell sorting apparatus, a target cell collection container, a residual solution collection container, and a control unit, wherein the continuous magnetic cell sorting apparatus comprising a rotating magnetic field generator, a forward solenoid and a reverse solenoid, the forward solenoid and the reverse solenoid surrounding the rotating magnetic field generator in forward and reverse directions, one end of the forward solenoid being connected to a solution outlet of the cell solution source, the other end of the forward solenoid being connected to one end of the reverse solenoid through a T-shaped tube, an inlet of the T-shaped tube being connected to an outlet of the forward solenoid, a first outlet of the T-shaped tube being connected to an inlet of the reverse solenoid, a second outlet of the T-shaped tube being connected to an inlet of the target cell collection container, the direction of the second outlet being consistent with the winding direction of the forward solenoid, the direction of the first outlet being opposite to the winding direction of the forward solenoid, and the control unit being connected to the continuous magnetic cell sorting apparatus and the solution driving device through control lines, and being configured to control the continuous magnetic cell sorting apparatus to generate a magnetic acting force and control the solution driving device to drive a solution in the cell solution source, so that unlabeled cells and magnetically labeled cells respectively flow into the residual solution collection container and the target cell collection container through the T-shaped tube.

2. The magnetic cell sorting system according to claim 1, wherein starting parts of the inlet, the first outlet and the second outlet of the T-shaped tube are provided with flow-stopping switches.

3. The magnetic cell sorting system according to claim 1, further comprising a device that is connected with the second outlet of the T-shaped tube and is for applying a negative pressure to the second outlet.

4. The magnetic cell sorting system according to claim 1, wherein the solution driving device uses solution line peristaltic driving, and comprises a primary solution pump arranged between the cell solution source and the continuous magnetic cell sorting apparatus and a secondary pump arranged between the continuous magnetic cell sorting apparatus and the target cell collection container.

5. The magnetic cell sorting system according to claim 1, wherein the control unit comprises a solution flow velocity controller connected to the solution driving device and a magnetic field controller connected to the continuous magnetic cell sorting apparatus through the control lines, and the solution flow velocity controller and the magnetic field controller controls the unlabeled cells and the magnetically labeled cells to move in opposite directions at the second outlet of the T-shaped tube to complete sorting of the magnetically labeled cells.

6. A treatment device, comprising the magnetic cell sorting system according to claim 1.

7. A magnetic cell sorting apparatus, comprising a rotating magnetic field generator, a forward solenoid and a reverse solenoid, the forward solenoid and the reverse solenoid surrounding the rotating magnetic field generator in forward and reverse directions, one end of the forward solenoid being connected to a solution outlet of a cell solution source, the other end of the forward solenoid being connected to one end of the reverse solenoid through a T-shaped tube, an inlet of the T-shaped tube being connected to an outlet of the forward solenoid, a first outlet of the T-shaped tube being connected to an inlet of the reverse solenoid, a second outlet of the T-shaped tube being connected to an inlet of a target cell collection container, the direction of the second outlet being consistent with the winding direction of the forward solenoid, and the direction of the first outlet being opposite to the winding direction of the forward solenoid.

8. The magnetic cell sorting apparatus according to claim 7, wherein starting parts of the inlet, the first outlet and the second outlet of the T-shaped tube are provided with flow-stopping switches.

9. The magnetic cell sorting apparatus according to claim 7, further comprising a device that is connected with the second outlet of the T-shaped tube and is for applying a negative pressure to the second outlet.

* * * * *